United States Patent [19]

Hall et al.

[11] Patent Number: 4,687,523
[45] Date of Patent: Aug. 18, 1987

[54] METHOD FOR CLEANING A CORE SAMPLE FROM A SUBTERRANEAN FORMATION OF SOLID CONTAMINANT PARTICLES

[75] Inventors: Arthur C. Hall, Dallas; E. Frank Schultz, Arlington; Ludwig D. Wiener, Dallas, all of Tex.

[73] Assignee: Mobil Oil Corporation, New York, N.Y.

[21] Appl. No.: 890,989

[22] Filed: Jul. 30, 1986

Related U.S. Application Data

[63] Continuation of Ser. No. 766,384, Aug. 16, 1985.

[51] Int. Cl.$^4$ .............................................. B08B 30/00
[52] U.S. Cl. .................................................... 134/30
[58] Field of Search ...................... 73/863, 38; 134/10, 134/11, 25.1, 30, 31, 39, 40

[56] References Cited

U.S. PATENT DOCUMENTS

| | | | |
|---|---|---|---|
| 2,371,645 | 3/1945 | Aitchison et al. ..................... | 134/31 |
| 2,617,719 | 11/1952 | Stewart ................................... | 73/38 |
| 3,325,309 | 6/1967 | Sutula et al. .......................... | 134/30 |
| 3,839,899 | 10/1974 | McMillen ................................ | 73/38 |
| 4,380,930 | 4/1983 | Podhrasky et al. ................... | 73/594 |

FOREIGN PATENT DOCUMENTS 0047956  3/1982  European Pat. Off. ............. 134/11

Primary Examiner—Stewart J. Levy
Assistant Examiner—Robert R. Raevis
Attorney, Agent, or Firm—Alexander J. McKillop; Michael G. Gilman; George W. Hager, Jr.

[57] ABSTRACT

A core sample from a subterranean formation is injected with an aqueous fluid and a pressurized gas which is soluble in the aqueous fluid. The fluid pressure is maintained within the core sample for a predetermined soak period. The core sample is then rapidly depressurized to atmospheric pressure so that gas is very rapidly or dynamically evolved out of solution within the core sample and rapidly transports solid contaminant particles to the outer surface of the core sample where they may be removed.

2 Claims, 2 Drawing Figures

METHOD FOR CLEANING A CORE SAMPLE FROM A SUBTERRANEAN FORMATION OF SOLID CONTAMINANT PARTICLES

This is a continuation of application Ser. No. 766,384, filed Aug. 16, 1985, now abandoned.

BACKGROUND OF THE INVENTION

In the production of minerals, specifically oil and gas, it is common to "engineer" the producing reservoir to improve the economic performance thereof. To do this, certain lithological properties of the reservoir must be determined, the two most important of these properties being the permeability and the porosity of the reservoir rock. Permeability is a measure of the ability of a material to transmit fluids through pore spaces of the mineral and is inversely proportional to the flow resistance offered by the material. Porosity of a material is defined as the ratio of the aggregate volume of its void or pore spaces to its gross bulk volume. In the case of an oil reservoir, porosity is a measure of the volume within the reservoir rock which is available for storing oil and gas.

Normally, porosity and permeability of a reservoir rock are determined from core samples by applying well-defined measurement procedures, such as those described on pages 660–669, *Petroleum Production Engineering-Development*, by L. C. Uren, Fourth Edition, McGraw-Hill Book Company, Inc., 1956.

Prior to carrying out such porosity and permeability measurements, as well as other desired measurements, it is the usual practice to clean the core sample of brine, salt deposits, residual hydrocarbons, and solid contaminant particles, such as rock microfragments and drilling mud solids. One of the standard cleaning methods is to flush the core sample with liquid toluene and carbon dioxide gas. The problem with this method is that carbon dioxide attacks the core sample itself. Other non-flushing methods have also been suggested and tried, such as ultrasonic cleaning. The present invention is directed to a new method for cleaning a core sample in which a dynamic evolution of a dissolved gas previously injected into the core sample in a liquid solution is utilized to carry solid contaminant particles from within the core sample to the outer surface of the core sample.

SUMMARY OF THE INVENTION

In accordance with the present invention, there is provided a method for the cleaning of a core sample from a subterranean formation by removal of solid contaminant particles. More particularly, a core sample is injected with an aqueous fluid and a pressurized gas which is soluble in the aqueous fluid. The fluid pressure within the core sample is maintained for a predetermined soak period. Thereafter, the core sample is rapidly depressurized to atmospheric pressure, such as by venting through a quick opening valve. In this manner, gas or vapor is dynamically evolved within the core sample and very rapidly transports the solid contaminant particles to the outer surface of the core sample where they may be removed. The method of this invention may be repeated as many times as necessary to obtain satisfactory cleaning of a particular core sample.

In a more specific aspect, a core sample placed in a pressure vessel is soaked with an ammonium hydroxide solution that is saturated with pressurized ammonia gas. After a predetermined soak period, the core sample is rapidly vented, as mentioned above, to allow the dynamically evolving ammonia gas to transport the solid contaminant particles to the outer surface of the core sample.

In carryng out the invention, the aqueous liquid and the pressurized gas may be mixed in a saturation vessel prior to injection into the core sample, or may be separately injected into the core sample wherein saturation of the aqueous liquid takes place within the core sample itself.

In a more specific aspect, the gas-saturated aqueous liquid is basic in nature, as opposed to acidic, so that it does not attack the carbonate material of the core sample itself. In one embodiment, the aqueous liquid is ammonium hydroxide, and the soluble gas is ammonia.

DESCRIPTION OF THE PREFERRED EMBODIMENT

Figure 1:
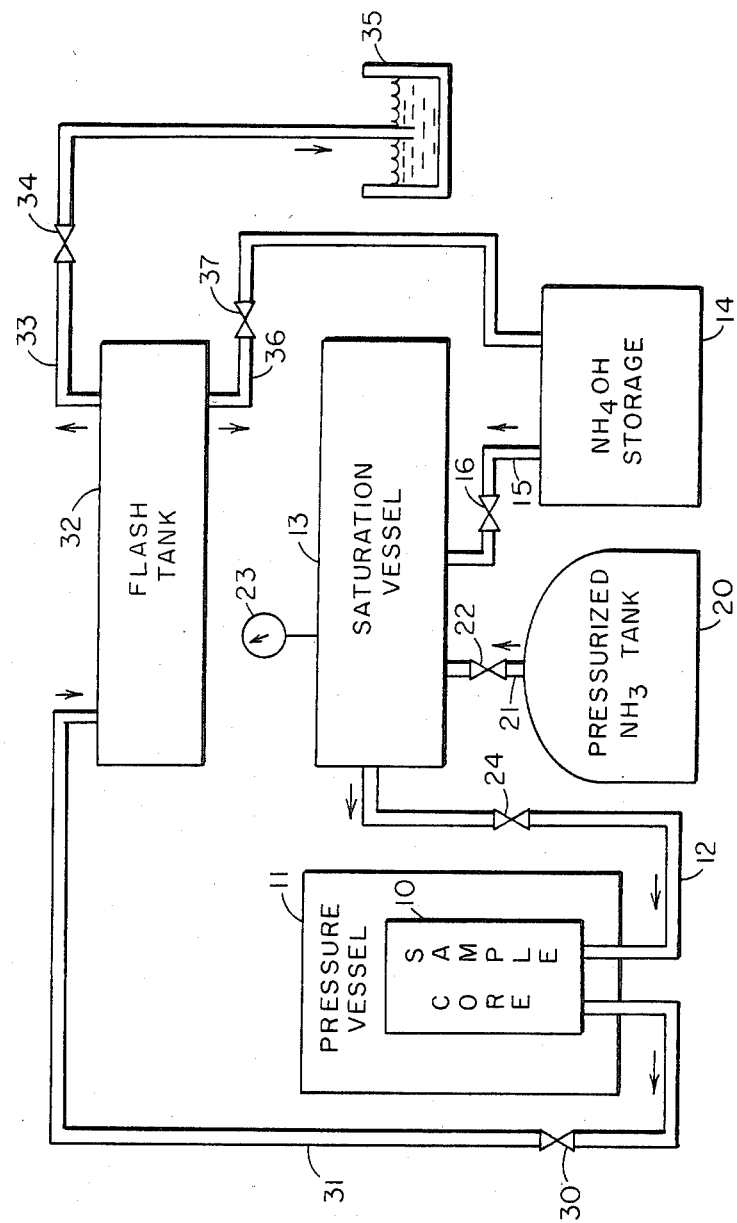
FIGS. 1 and 2 are schematic views of apparatus for cleaning a core sample by the dynamic evolution of gas or vapor to sweep out insoluble solid contaminant particles therefrom.

Referring now to FIG. 1, there is illustrated an apparatus for carrying out the method of the present invention of removing solid contaminant particles, such as rock microfragments and drilling mud solids, from pores and cavities within core samples obtained from subterranean formations during drilling for petroleum exploration and production.

A core sample 10 which is to be cleaned of solid contaminant particles is placed in a suitable pressure vessel 11. An aqueous fluid which is saturated with a soluble gas is injected under pressure into the core sample by way of line 12 leading from saturation vessel 13 to the core sample 10 inside the pressure vessel 11. Saturation vessel 13 serves as a mixer for the aqueous fluid and the pressurized gas. It provides a high surface area for the interaction of the aqueous fluid with the gas. Such high surface area may be provided by a gravel fill, high-surface area rings, or the like. The aqueous fluid, such as an ammonium hydroxide liquid, for example, is supplied to the saturation vessel 13 from a fluid storage tank 14 through flow line 15 and valve 16. Once the vessel is partially filled with the ammonium hydroxide, valve 16 is closed. At this time, ammonia gas from a pressurized tank or bottle 20 is supplied to saturation vessel 13 through flow line 21 and valve 22. Ammonia gas is typically bottled at 114 pounds of pressure and 72° F. When the ammonium hydroxide liquid is saturated with ammonia gas up to about 50 to 100 pounds of pressure, as indicated by pressure meter 23, valve 22 is closed to shut off the flow of ammonia gas.

The ammonium hydroxide liquid saturated with the pressurized ammonia gas is next injected into the core sample 10 through flow line 12 and valve 24. This aqueous fluid is allowed to soak in the core sample for a predetermined time period of about 10 to 15 minutes, for example. During this soak period, the ammonia attacks the clays of the drilling mud within the core sample and loosens them up or dissolves them to some extent. It will not attack the solid barite particles which form the weighting compound of the mud. Nothing is available which would dissolve the barite without also destroying the core sample. After the soak period, valve 30, such as a quick-opening ball valve, is opened to rapidly vent the pressurized gas from the core sample by way of flow line 31. The gas very rapidly evolves from solution to carry the solid contaminating barite and clay particles to the outer surface of the core sample where they can thereafter be removed by conventional flushing or mechanical means.

During this very rapid, dynamic evolution of gas, both the liquid ammonium hydroxide and ammonia gas are blown out of the core sample and collected in a flash tank 32. The ammonia gas can be bled off from the flash tank 32 through flow line 33 and valve 34 into a pond or water storage vessel 35 where water can absorb the excess gas. The ammonium hydroxide liquid can be recycled out of the flash tank through flow line 36 and valve 37 and back into the ammonium storge tank 14 for further use.

The core sample will most probably require several cycles of the cleaning process of the present invention to obtain a core sample sufficiently clean to determine an accurate measure of porosity and permeability. The apparatus described above provides for such recycling at a reasonably fast cycle rate. However, various configurations of such apparatus may be employed in carrying out the cleaning process of the invention. For example, the pressure vessel 11 for housing the core sample may be simply a piece of pipe threaded on each end for screw caps. Flow lines will pass through the piping, or caps, for use in the injection of the ammonium hydroxide and ammonia gas and for the release of the gas pressure. More sophisticated pressure vessels may be employed, such as those described in detail in U.S. Pat. No. 3,839,899 to J. M. McMillen and U.S. Pat. No. 4,380,930 to J. Podhrasky and E. S. Sprunt, for example.

Although a saturation vessel 13 has been described above for use in the mixing of the ammonium hydroxide liquid and ammonia gas, such vessel can be dispensed with and the mixing allowed to take place within the core sample itself. The ammonium hydroxide liquid can be injected directly into the core sample from the storage tank 14. Thereafter, the ammonia gas can also be injected directly into the core sample from the pressurized tank 20 where it bubbles through the core sample and mixes with the ammonium hydroxide.

It is also a specific feature of the invention to provide a gas that is basic in nature, as opposed to acidic. Certain types of core samples, calcium carbonate cores, for example, would be attacked and destroyed by an acidic solution of gas, such as a carbon dioxide. A basic solution of gas, such as ammonium hydroxide, will not attack the calcium carbonate core sample. Consequently, the ammonium hydroxide saturated with ammonia gas allows the desired core cleaning process to take place by very rapid or dynamic evolution of ammonia gas without destroying the core sample in the process.

In a yet further aspect of the invention, a preliminary step may be carried out of cleaning the core sample to remove from pores and cavities adjacent to the exterior surface of the core sample any solid contaminant particles that have been allowed to dry in place and thereby interfere with the cleaning of solid contaminant particles from the interior of the core sample. This may be accomplished by soaking and/or washing the core sample with a 0.1 normal caustic solution, or with a 0.1 normal ammonium hydroxide solution.

Figure 2:
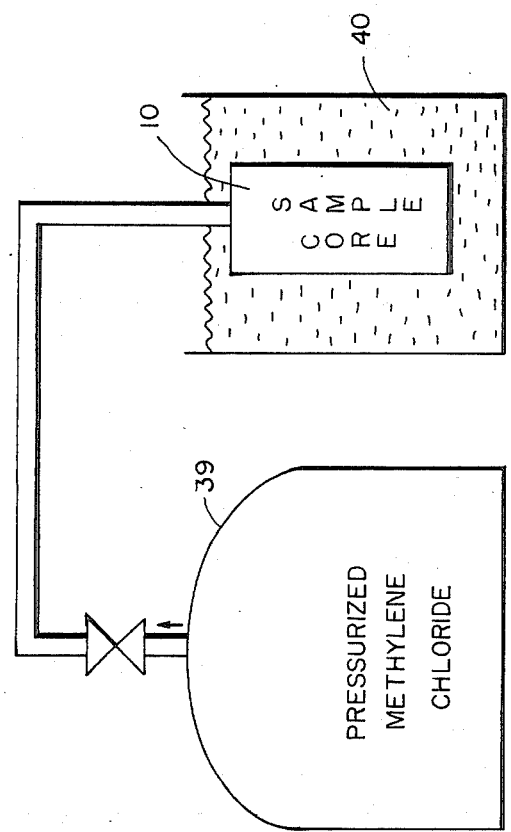

An alternative to the cleaning of a core sample by the injection of an aqueous liquid with a soluble pressurized gas, such as ammonium hydroxide and ammonia gas, and the subsequent pressure release is the injection of a volatile organic liquid, such as methylene chloride, under pressure with a subsequent rapid application of heat as shown in FIG. 2. This heat may be applied by suddenly immersing the core sample 10, filled with the volatile organic liquid from pressurized tank 39, into a heated liquid medium 40, such as boiling water. When the temperature rises within the core to the point of combustion, there is with this alternative injection an explosive evolution of gas which likewise sweeps out solid contaminant particles from within the core sample to the outer surface of the core sample.

While the foregoing has described the core cleaning method of the present invention employing the dynamic evolution of a gas from within the core sample itself, it is to be understood that various modifications to the disclosed embodiment may become apparent to one skilled in the art without departing from the scope and spirit of the invention as set forth in the appended claims.

We claim:

1. A method for cleaning a core sample from a subterranean formation of solid contaminant particles, comprising the steps of:
   (a) filling said core sample under pressure with a volatile organic liquid in which said solid contaminant particles are insoluble,
   (b) rapidly heating said liquid-filled core sample by immersion into a heated medium to dynamically evolve gas or vapor from said heated organic liquid to thereby sweep said insoluble solid contaminant particles from within said core sample to the outer surface of said core sample, and
   (c) removing said solid contaminant particles from the outer surface of said core sample.

2. The method of claim 1 wherein said heated medium is boiling water.

* * * * *